United States Patent [19]

Linck, II et al.

[11] 4,030,197

[45] June 21, 1977

[54] BASE PLATES FOR DENTAL ARTICULATORS

[75] Inventors: Donald W. Linck, II, Pleasant Hill; George Kaprelian, Sunnyvale, both of Calif.

[73] Assignees: Donald W. Linck, II, Pleasant Hill; George Kaprelian, Sunnyvale; Tom Basta, Cupertino; Maury Corbett, San Jose; William Danzig, Walnut Creek; Gary Hunt, San Mateo; Arthur Ingram, Fremont; Charles McNeill, Walnut Creek; Gerald Preiner, Burlingame; Ronald Roth, San Mateo, all of Calif.

[22] Filed: May 14, 1976

[21] Appl. No.: 686,541

[52] U.S. Cl. .................................................. 32/32
[51] Int. Cl.² ........................................ A61C 11/00

[58] Field of Search .............. 32/32, 11, 19, 20, 21, 32/71

[56] References Cited

UNITED STATES PATENTS

| | | | |
|---|---|---|---|
| 2,621,407 | 12/1952 | Schlesinger | 32/32 |
| 2,629,929 | 3/1953 | Levine et al. | 32/32 |

*Primary Examiner*—Robert Peshock
*Attorney, Agent, or Firm*—Thomas Schneck, Jr.

[57] ABSTRACT

A base plate mountable in a dental articulator, having a groove forming a closed curve therein. The groove defines a base plate of a smaller size, such that the larger base plate, containing the groove, may be fractured along the groove and a smaller base plate may be used in lieu of the larger one.

10 Claims, 7 Drawing Figures

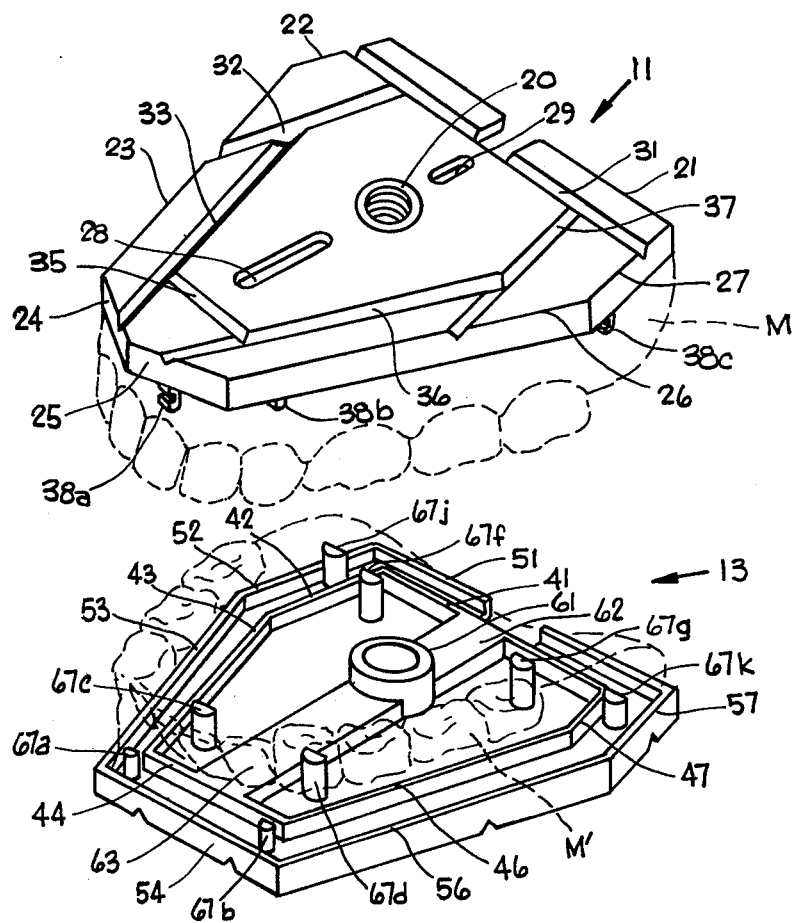
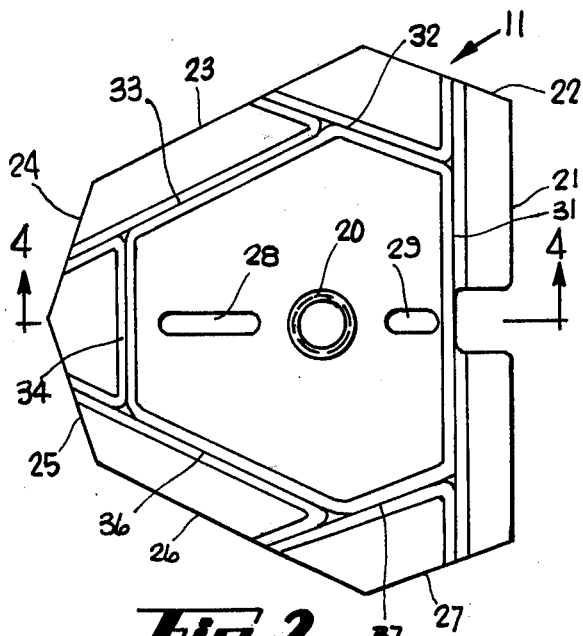
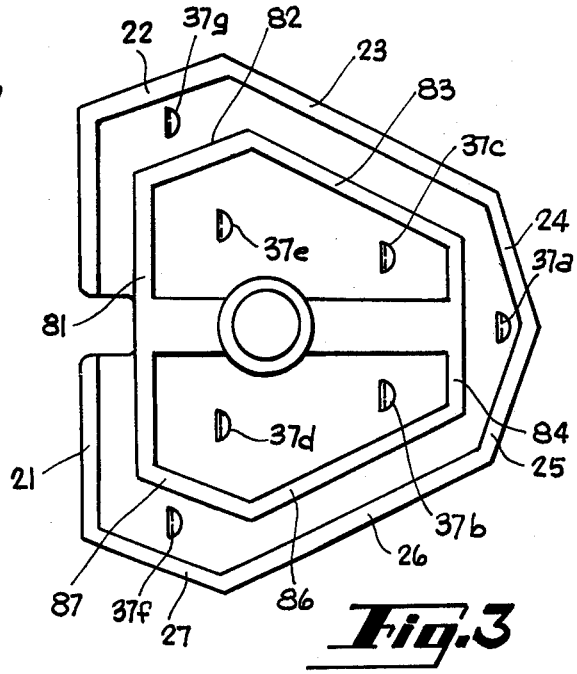

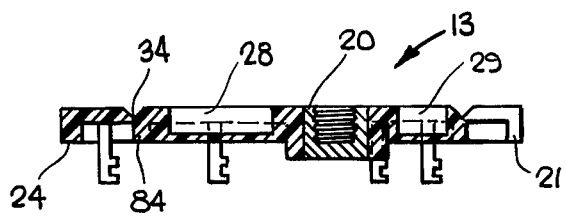
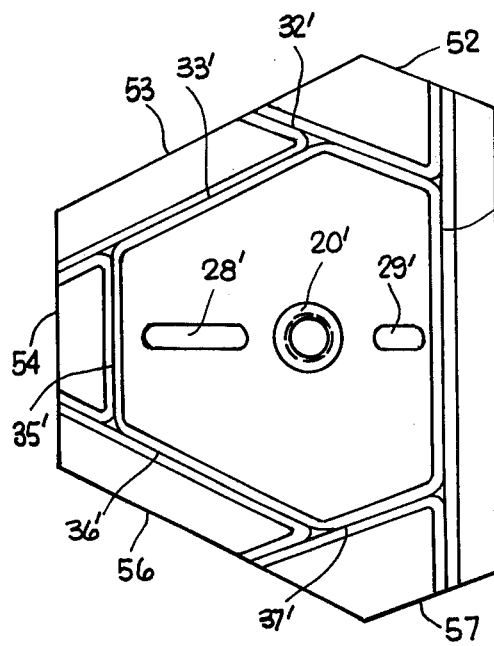
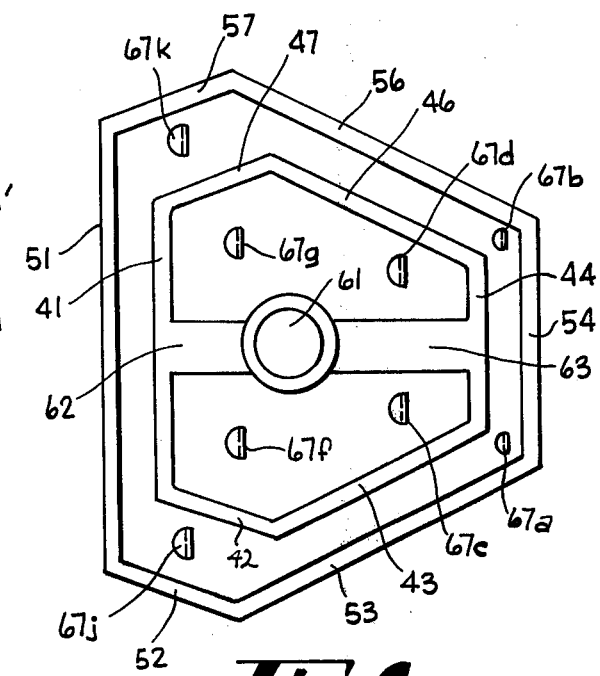
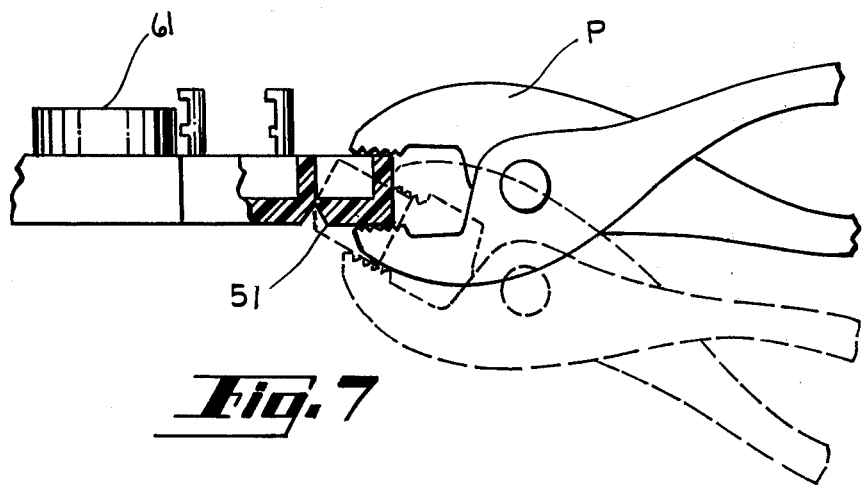

BASE PLATES FOR DENTAL ARTICULATORS

BACKGROUND OF THE INVENTION.

a. Field of the Invention

The invention relates to apparatus used with dental articulators, and more particularly to base plates, known as rings, for attachment to plaster models which are held in articulators.

b. Prior Art

In making models of patients' teeth, dentists commonly use a tray, with an impression material therein, to obtain an impression of a patient's teeth. Once the impression is made, a model may be made, simulating the patient's teeth. Plaster material is added to simulate a patient's gums and a base plate, previously known as a ring, is added above the gum portion of the model so that the model may be mounted in an articulator which provides simulation of human jaws so that the patient's bite, as well as other characteristics, may be studied.

The base plates, or rings, of the prior art were generally made of metal, typically cast aluminum. The problem with such castings is that they are relatively expensive. Moreover, one size ring is used by dentists and another size which is larger, was not available for orthodontists.

It is desirable to keep a base plate with a dental model so that the model will be mounted in an articulator in the same manner each time. However, some dentists are inclined to remove base plates and reuse them because of their cost. This creates a problem if the model is used again in an articulator.

It is an object of our invention to provide a base plate for dental models which is useful for both dentists and orthodontists and which is relatively inexpensive.

SUMMARY OF THE INVENTION

The above object is achieved with a base plate of a first size having an outer periphery and a central region having a ferrule for mounting the central region to an articulator, together with a groove in the shape of a closed curve between the central region and the outer periphery. The shape of the groove defines a base plate of a smaller size and is of such a depth for promoting material fracture along the groove upon mechanical stressing, in preference to fracture elsewhere in the base plate. The groove is formed by intersecting segments extending to the outer periphery of the larger base plate and material fracture in unwanted regions is prevented by ribs adjacent to the groove which tend to keep the material from fracturing transverse to the ribs, except where a groove crosses a rib.

BRIEF DESCRIPTION OF THE DRAWINGS

FIG. 1 is a perspective view of a pair of base plates of the present invention, shown in respective planes in which the base plates would be mounted in a dental articulator.

FIG. 2 is a bottom view of the upper base plate shown in FIG. 1.

FIG. 3 is a top view of the apparatus of FIG. 2.

FIG. 4 is a side sectional view taken along the line 4—4 in FIG. 2.

FIG. 5 is a top view of the lower base plate shown in FIG. 1.

FIG. 6 is a bottom view of the apparatus shown in FIG. 5.

FIG. 7 is a side sectional view of a base plate of the present invention, showing a manner of fracturing a base plate along a groove therein.

DESCRIPTION OF THE PREFERRED EMBODIMENT

In the perspective of FIG. 1, an upper base plate 11 is seen spaced apart from a lower base plate 13. Upper base plate 11 is seen to have an outer periphery defined by edges 21, 22, 23, 24, 25, 26 and 27, which will be seen to include rib segments, as shown in FIG. 3. The upper base plate also has a central region including a threaded ferrule 20 which is used as a mounting means for attaching the base plate to an articulator. Channels 28 and 29 are used for orienting the base plate with respect to the articulator.

Between the central region of the base plate where ferrule 20 is disposed and the outer periphery thereof, a groove is created, forming a closed curve defining a base plate of a smaller size in comparison to the outer periphery of the larger base plate 11 wherein said groove is defined. The groove is defined by the intersecting groove segments 31, 32, 33, 34, 35, 36 and 37. The segments extend to the outer periphery of the base plate and are intended to promote material fracture along the groove, upon mechanical stressing, in preference to material fracture in base plate regions other than where groove segments are disposed.

Lugs 38a, 38b and 38c extend downwardly from the bottom of upper base plate 11. The lugs extend downwardly approximately ¼ inch from the top of base plate 11. Lugs 38a, 38b and 38c have protrusions or bumps thereon which assist in anchoring the lugs into the dental model M, indicated by the phantom lines. The upper base plate 11 is pressed into model M after the model has been cast, but before the plaster of the model has set. Once the plaster sets, a plurality of lugs in the base plate anchors the base plate to the model so that the model may be mounted in a dental articulator.

The inward side of base plate 13 may be seen in the lower portion of FIG. 1. The central portion of lower base plate 13 includes the capped end 61 of a ferrule 20 with channel housings 62, 63 extending radially outwardly. Channel housings 62, 63 are thickened base plate regions wherein channels are defined in the opposite side of the base plate for orienting the base plate in an articulator. The channel housings 62, 63 terminate at a first rib defined by the rib segments 41, 42, 43, 44, 46 and 47. The rib segments are disposed adjacently inward from the groove on the other side of the base plate for strengthening the base plate adjacent to the groove.

A second rib, generally congruent with the first rib, but radially outwardly spaced therefrom can be seen to be defined by the rib segments 51, 52, 53, 54, 56 and 57. It will be seen that the two ribs are congruent, although this is not critical because one rib may include rib segments which differ slightly from the geometry of the other rib.

The upwardly extending lugs 67a, 67b, 67c, 67d, 67e, 67f, 67g, 67j and 67k serve to anchor the base plate to a model M', as previously described with respect to model M held to the upper base plate 11.

In FIG. 2, the upper base plate 11 may be seen from its outward side. The base plate may be seen to have central region including ferrule 20, a pair of channels 28, 29 which are slightly elongated indentations in the base plate for orienting or indexing the base plate with respect to studs fitting into these indentations in an articulator. A rib is at the outer periphery of base plate 13 and this rib is defined by the rib segments 21, 22, 23, 24, 25, 26 and 27 which are more clearly visible in FIG. 3. Between the central region of ferrule 20 and the outer periphery of the base is a groove in the base which is a closed curve defined by the groove segments 31, 32, 33, 34, 36 and 37. Adjacent groove segments intersect each other and extend to the outer periphery of the base, at least on one end thereof. As mentioned previously, the grooves are intended to promote material fracture along the groove, upon mechanical stressing, in preference to material fracture in base plate regions other than where the groove is disposed.

FIG. 3 is an inward view of base plate 13. The first rib defined by rib segments 81, 82, 83, 84, 86 and 87 is positioned slightly radially inward from the groove on the other side of the base plate, preferably adjacent to the inward edge of the groove. The first and second ribs of the base plate, together with the groove, essentially define two base plates, one of greater size, the other of lesser size. As mentioned previously, the second, and larger rib is defined by rib segments 21, 22, 23, 24, 25, 26 and 27.

The following dimensions characterize the inner and outer ribs.

TABLE I

| Rib (outer side) | Length (inches) |
| --- | --- |
| 51 | 2-7/8 |
| 52 | 1 |
| 53 | 2 |
| 54 | 15/16 |
| 41 | 2 |
| 42 | 13/16 |
| 43 | 1-5/8 |
| 44 | 1-1/8 |

The dimensions of Table I are exemplary and are not critical.

From the section of FIG. 4, further construction details of the base plate may be seen. Ferrule 20 may be seen to be made of metal and threaded. In practice, the base plate is made out of injection molded plastic around ferrule 20. In other words, a cold ferrule is placed in a mold and molten plastic is injected around it. As the plastic cools, it shrinks around the ferrule, holding it firmly in place. A threaded metal ferrule is advantageous, compared to a threaded plastic structure, inasmuch as the metal threads will provide precision mounting of the base plate to the articulator. Moreover, the metal threads of ferrule 20 are less subject to wear than plastic threads would be.

Ribs 24, 84, and 21, as well as the other ribs, are typically ¼ inch in thickness from the outer side of a base plate to the inward side. The thickness of ferrule 20 is approximately ⅜ inch, while the diameter of the metal portion of the ferrule is approximately 7/16 inch, although these dimensions are not critical. The thickness of the base plate in areas where there are not ribs is approximately 3/32 inch and the depth of a groove at the base thereof is approximately 0.015 inches. The material of the base plate is a brittle styrene which can be fractured by hand or with a tool yet strong enough to allow the lugs projecting therefrom to hold the plaster. In practice, a styrene having a 7,000 pound notching strength is preferred. This notching strength is important in characterizing the brittleness of the material necessary to allow fracture along the groove of the base plates.

FIGS. 5 and 6 show outward and inward views respectively of the upper base plate 13. Base plate 13 generally has the same characteristics as the upper base plate 11 having a groove defined by groove segments, in FIG. 5, 31', 32', 33', 35', 36' and 37' which, when fractured, defines a baseplate of a smaller size, having a periphery defined by rib segments 41, 42, 43, 44, 46 and 47, in FIG. 6. The larger, unfractured base plate has an outer periphery defined by rib segments 51, 52, 53, 54, 56 and 57. The rib segments have dimensions which are similar to the dimensions of corresponding ribs of base plate 11, exemplified in Table I. The base plates are generally the same except that the forward outer rib segment 54 is parallel to the rearward rib segment 51, compared to the forward V-shaped segments 24, 25 of an upper base plate in FIGS. 2 and 3.

FIG. 8 illustrates use of the breakaway base plates of the present invention. A tool such as the pliers, P, can be used to fracture an outer base plate portion at the groove segment 51. This procedure is repeated for however many base plate segments it is desired to remove.

The larger base plate is usually preferred by orthodontists and by dental practitioners who wish to compensate facial asymmetries that patients may have. The smaller base plate is preferred in general dentistry and for use by gnathologists. The expense of the plastic base plates is such that they can be maintained with a patient's models so that a permanent record may be maintained, rather than remounting base plates each time the models are used with the articulator.

The general parallel structure of inner and outer ribs promotes rigidity of the base plates. At the same time, an advantage of utilizing plastic is that the base plates may be trimmed and shaped easier than metal rings of the prior art, so that grinding wheels are not broken or worn as quickly.

A further advantage is that the ferrule has a relatively deep threaded area compared to the thickness of the base plate. As can be seen in FIG. 4, the threaded section of ferrule 20 exceeds the thickness of the ribs. This permits secure mounting to dental articulators.

A further advantage of the present apparatus is that the ribs which secure dental models are generally flat and it is easier to mount plaster to such flat ribs, than round edges which characterize rings of the prior art.

The words "inner" and "outer" referring to the two sides of the upper and lower base plates are intended to have meaning relatively to the mounting of base plates in an articulator and are not intended for use in any absolute sense.

We claim:

1. A breakaway base plate for mounting dental models in articulators comprising, a base plate of a first size having an outer periphery, a central region having means for mounting said central region to an articulator, and a groove in said base plate between said central region and said outer periphery, said groove forming a closed curve defining a base plate of a second size, smaller than said first size, and having a groove profile for promoting material fracture along said groove, upon mechanical stressing, in preference to material fracture in base plate regions other than where said groove is disposed.

2. The apparatus of claim 1 wherein a first rib is disposed adjacently inward from said groove, thereby strengthening said base plate adjacent to said groove.

3. The apparatus of claim 2 wherein a second rib is disposed about the periphery of said base thereby strengthening said base plate adjacent to said periphery.

4. The apparatus of claim 3 wherein said first and second ribs are disposed on a side of said base plate which is the same side in which said groove is defined.

5. The apparatus of claim 1 wherein said groove is defined by intersecting segments which extend to the outer periphery of said base plate.

6. The apparatus of claim 1 wherein said mounting means comprises a ferrule.

7. The apparatus of claim 6 wherein said ferrule is metal held in fixed relation to said base plate, which is plastic.

8. The apparatus of claim 6 wherein said mounting means further includes a pair of spaced indexing channels for orientation in an articulator.

9. The apparatus of claim 1 further defined by a plurality of spaced apart upwardly projecting studs for anchoring a dental model to said base plate.

10. A pair of breakaway base plates for mounting models of upper and lower teeth in an articulator comprising, upper and lower, spaced apart, base plates of approximately equal first size, each base plate having an outer periphery, a central region having means for mounting said central region to an articulator, and a groove in said base plate between said central region and said outer periphery, said groove forming a closed curve defining a base plate of a second size, smaller than said first size, and having a groove profile for promoting material fracture along said groove, upon mechanical stressing, in preference to material fracture in base plate regions other than where said groove is disposed, each base plate having mutually facing, spaced apart, studs for anchoring models of upper and lower teeth to respective upper and lower base plates.

* * * * *